United States Patent
Park

(10) Patent No.: US 6,881,192 B1
(45) Date of Patent: Apr. 19, 2005

(54) MEASUREMENT OF SLEEP APNEA DURATION AND EVALUATION OF RESPONSE THERAPIES USING DURATION METRICS

(75) Inventor: Euljoon Park, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 295 days.

(21) Appl. No.: 10/170,384

(22) Filed: Jun. 12, 2002

(51) Int. Cl.[7] .................................................. A61B 5/08
(52) U.S. Cl. ...................... 600/529; 600/484; 600/501; 607/17; 607/42
(58) Field of Search .................................. 600/300, 301, 600/484, 508–525, 529–543, 595; 607/1–6, 17–20, 119, 42

(56) References Cited

U.S. PATENT DOCUMENTS

| | | | |
|---|---|---|---|
| 4,846,195 A | * 7/1989 | Alt | 600/595 |
| 5,398,682 A | 3/1995 | Lynn | |
| 5,769,084 A | 6/1998 | Katz et al. | |
| 5,891,023 A | 4/1999 | Lynn | |
| 5,944,680 A | 8/1999 | Christopherson et al. | |
| 5,974,340 A | * 10/1999 | Kadhiresan | 607/18 |
| 6,091,973 A | 7/2000 | Colla et al. | |
| 6,126,611 A | * 10/2000 | Bourgeois et al. | 600/529 |
| 6,223,064 B1 | 4/2001 | Lynn et al. | |
| 6,342,039 B1 | 1/2002 | Lynn et al. | |
| 6,368,287 B1 | 4/2002 | Hadas | |
| 6,589,188 B1 | * 7/2003 | Street et al. | 600/538 |
| 6,641,542 B1 | 11/2003 | Cho et al. | 600/529 |
| 6,731,984 B1 | * 5/2004 | Cho et al. | 607/17 |
| 2001/0018557 A1 | 8/2001 | Lynn et al. | |

FOREIGN PATENT DOCUMENTS

| | | |
|---|---|---|
| WO | 99/34864 | 7/1999 |
| WO | 00/01438 | 1/2000 |

OTHER PUBLICATIONS

Park, E. et al., "Heart Failure Assessment with Impedance Respiration Sensor", EUROPACE 2001, Copenhagen, Denmark, Jun. 24–27, 2001, pp. 561–565.

* cited by examiner

Primary Examiner—Robert L. Nasser
Assistant Examiner—Patricia Mallari

(57) ABSTRACT

An implantable cardiac device is programmed to detect an episode of sleep apnea, measure the duration of the episode, and store this information in memory. When multiple episodes are recorded, the device computes statistics on the apnea durations, such as average apnea duration and total apnea duration for a preselected time period (e.g., 8-hour rest period, 24-hour day, etc.). The implantable cardiac device may further be used to administer pacing therapy in response to detecting sleep apnea. Under the control of a physician, the implantable device may be programmed to administer different types of responsive therapies to evaluate whether certain therapies are more effective at treating apnea than others. For instance, a pacing therapy that results in lowering the average apnea duration or total apnea duration may be preferred over other pacing therapies that do not achieve such results.

48 Claims, 6 Drawing Sheets

(12) United States Patent
US 6,881,192 B1

MEASUREMENT OF SLEEP APNEA DURATION AND EVALUATION OF RESPONSE THERAPIES USING DURATION METRICS

TECHNICAL FIELD

The present invention generally relates to implantable cardiac devices, and particularly, to techniques for measuring duration of sleep apnea episodes and using apnea duration measurements to evaluate the effectiveness of various pacing therapies administered in response to sleep apnea.

BACKGROUND

Sleep apnea is a condition in which a person stops breathing for a short time while sleeping. Sleep apnea has multiple classifications based on the source of dysfunction. Obstructive sleep apnea results from mechanical blockage of the airway, for example, due to weight of fatty neck tissue compressing the trachea. Central sleep apnea results from neurological dysfunction. Mixed sleep apnea has a combination of mechanical and neurological cause.

Symptoms of sleep apnea include snoring, breath holding during sleep, rapid awakening with gasping for air, morning headaches, depression, irritability, loss of memory, lack of energy, high risk of automobile and workplace accidents, and lack of high quality sleep and resulting daytime grogginess and sleepiness. Sleep apnea is rarely fatal but is linked to high blood pressure and increased probability of heart disease, stroke, and arrhythmias. Patients with coronary artery disease who have a blood oxygen level lowered by sleep-disordered breathing may be at risk of ventricular arrhythmia and nocturnal sudden death. Furthermore, sleep-disordered breathing may cause coronary artery disease and hypertension.

Various treatments exist for sleep apnea including medical device treatments, surgery, and drugs. The type of treatment depends on the type of sleep apnea. For patients who also experience heart failure or other cardiac conditions, another form of treatment that has been proposed for treating sleep apnea is pacing therapy administered by an implantable cardiac device, such as an implantable pacemaker. For this latter form of treatment, however, there remains a need to further improve the operation of implantable cardiac devices to better analyze sleep apnea and determine which types of response therapies offer more effective results.

SUMMARY

An implantable cardiac device is programmed to detect an episode of sleep apnea and measure the duration of the episode. In one implementation, the implantable cardiac device initially confirms that a patient is at rest using an activity sensor or posture sensor. It then monitors a respiration-related parameter (e.g., respiration rate, tidal volume, minute ventilation) or oxygen-related parameter ($O_2$ saturation, $SO_2$, $O_2$ pressure) to determine when the patient is experiencing a sleep apnea episode. The cardiac device measures the duration of the episode and stores the duration. When durations for multiple episodes are recorded, the device computes statistics, such as average apnea duration and total apnea duration for a preselected time period (e.g., 8-hour rest period, 24-hour day, etc.).

The implantable cardiac device may be configured to administer pacing therapy (or other therapies) in response to detecting sleep apnea. Under the control of a physician, the implantable device may be programmed to administer different types of responsive pacing therapies and then use the apnea duration statistics to help evaluate whether certain therapies are more effective at treating apnea than others. For instance, a pacing therapy that results in lowering the average apnea duration or total apnea duration may be preferred over other pacing therapies that do not achieve such results.

DETAILED DESCRIPTION

Overview

Today, physicians use the apnea hypopnea index (AHI) as the standard index for describing the severity of sleep apnea. AHI is based on the number of apnea episodes a patient experiences in a predetermined time period (e.g., an 8 hour rest period, or a 24-hour period). Apnea episodes with different duration are counted equally.

In the following discussion, an implantable cardiac device is described that utilizes a different metric for describing severity of sleep apnea. Namely, the device is programmed to measure durations of each episode of sleep apnea and perform statistical analysis on the recorded durations to determine such metrics as average apnea duration or total apnea duration for a given time period (e.g. resting period, 24 hour period, etc.). The device can then be programmed to administer different pacing therapies and evaluate which pacing therapies are effective at reducing sleep apnea duration. In this manner, the apnea duration metrics derived by the implantable cardiac device can be used to prescribe effective pacing treatments.

Implantable cardiac devices are commonly characterized as a miniature computing device that is implanted into the body of a patient to monitor, regulate, and/or correct heart activity. Such devices include implantable cardiac stimulation devices (e.g., implantable cardiac pacemakers, implantable defibrillators) that apply stimulation therapy to the heart as well as implantable cardiac monitors that monitor and record heart activity for diagnostic purposes. The following discussion describes first an exemplary cardiac device and then a mode of operation in which sleep apnea episodes are detected, their durations are measured, and various pacing therapies are evaluated.

Exemplary Implantable Cardiac Device

Figure 1:
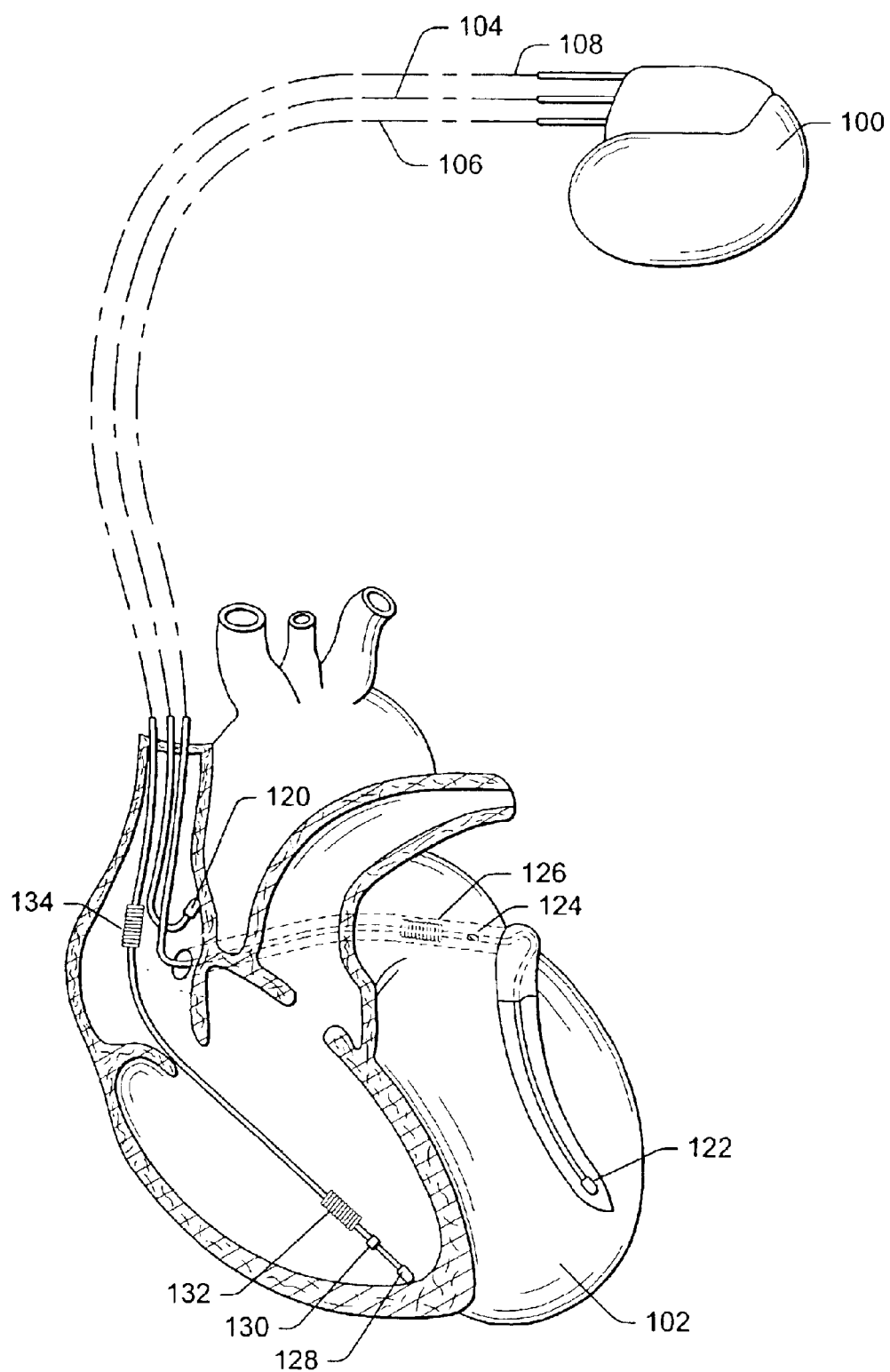
FIG. 1 is a diagrammatic illustration of an implantable cardiac device in electrical communication with a patient's heart for multi-chamber sensing and delivery of multi-chamber stimulation and shock therapy.

FIG. 1 shows an exemplary implantable cardiac device 100 in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage. The right atrial lead 104 enables the device to sense atrial cardiac signals and apply pacing therapy to the right atrial chamber.

The coronary sinus lead 106 positions a left ventricular tip electrode 122 & adjacent to the left ventricle and/or additional electrode(s) adjacent to the left atrium, such as a left atrial ring electrode 124 and a left atrial coil electrode 126. The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
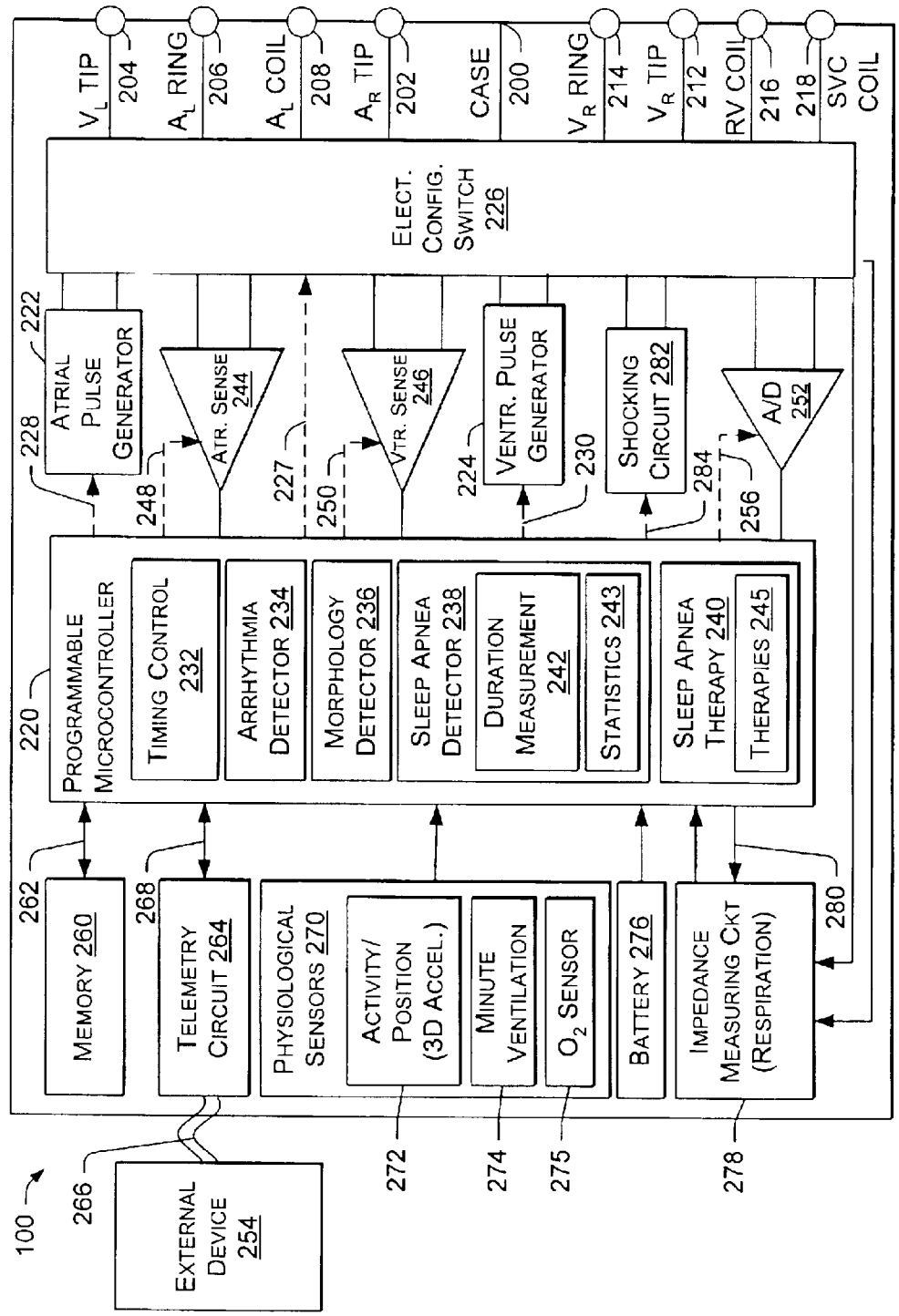
FIG. 2 is a functional block diagram of the multi-chamber implantable cardiac device.

FIG. 2 shows an exemplary, simplified block diagram depicting various components of the implantable cardiac device 100. The components are housed in housing 200, which is often referred to as the "can", "case", "encasing", or "case electrode", and may be programmably selected to act as the return electrode for unipolar modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals), including:

a right atrial tip terminal ($A_R$ TIP) 202 for atrial tip electrode 120;

a left ventricular tip terminal ($V_L$ TIP) 204 for left ventricular tip electrode 122;

a left atrial ring terminal ($A_L$ RING) 206 for left atrial ring electrode 124;

a left atrial shocking terminal ($A_L$ COIL) 208 for left atrial coil electrode 126;

a right ventricular tip terminal ($V_R$ TIP) 212 for right ventricular tip electrode 128;

a right ventricular ring terminal ($V_R$ RING) 214 for right ventricular ring electrode 130;

a right ventricular shocking terminal (RV COIL) 216 for RV coil electrode 132; and an SVC shocking terminal (SVC COIL) 218 for SVC coil electrode 134.

The implantable cardiac device 100 includes a programmable microcontroller 220 that controls various operations of the ICTD, including cardiac monitoring and stimulation therapy. Microcontroller 220 includes a microprocessor (or equivalent control circuitry), RAM and/or ROM memory, logic and timing circuitry, state machine circuitry, and I/O circuitry.

Device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, combipolar, etc.) by selectively closing the appropriate combination of switches. To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (A—A) delay, or ventricular interconduction (V—V) delay, etc.). The timing control circuitry may also be used for the timing of refractory periods, blanking intervals, noise detection windows, evoked response windows, alert intervals, marker channel timing, and so on.

Microcontroller 220 is also equipped with an arrhythmia detector 234, a morphology detector 236, a sleep apnea detector 238, and a sleep apnea therapy module 240. The sleep apnea detector 238 is configured to detect episodes of sleep apnea that occur while the patient is at rest. In one implementation, the sleep apnea detector 238 uses changes in respiration-related data to detect episodes of sleep apnea. Such respiration-related data might include, for example, respiration rate, tidal volume, minute ventilation, respiration signal amplitude, and the like.

The sleep apnea detector 238 implements a duration measurement module 242 that measures duration of each sleep apnea episode. The duration measurement module 242 includes a timer or counter that is started when the detector 238 determines that the patient is experiencing a sleep apnea episode and is stopped when the patient recovers from the episode. In one implementation, the detector 238 utilizes a pair of thresholds to detect when a patient's breathing pattern exhibits an episode of hyperventilation (i.e., a respiration signal exceeds an upper threshold) followed by an episode of sleep apnea (i.e., the respiration signal remains below a lower threshold). The measurement module 240 measures the time starting when the signal crosses below the lower threshold, without subsequently moving above the lower threshold for a predetermined time period, until the time when the signal once again crosses above the lower threshold.

The sleep apnea event and duration are then recorded in the device memory. A statistical analysis module 243 is employed to compute various statistics on the collected apnea episodes. For instance, the statistical module 243 can derive the average episode duration for the patient and the total duration of all episodes experienced by the patient during a predefined time period (e.g., resting period, 24 hours, etc.).

The sleep apnea therapy module 240 prescribes one or more pacing therapies 245 that can be administered in response to detection of sleep apnea. For example, the therapies might include overdrive pacing in which the pacing rate is increased by some fixed or adjustable amount. The responsive pacing may be applied for a period of time, or a predetermined number of beats, or until the sleep apnea episode has concluded. The therapies might call for different degrees of gradually decreasing the pacing rate to the intrinsic rate of the resting patient. As will be described below in more detail, the sleep apnea therapy module 240 administers different therapies 245 during an evaluation timeframe and evaluates how each therapy affects the apnea duration metrics. For example, therapies that lower the average apnea duration or the total apnea duration are considered more effective than therapies that fail to lower these duration metrics.

The components 234–243 may be implemented in hardware as part of the microcontroller 220, or as software/firmware instructions programmed into the device and executed on the microcontroller 220 during certain modes of operation. Although not shown, the microcontroller 220 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 104, coronary sinus lead 106, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity. Each sensing circuit 244 and 246 may employ one or more low power, precision amplifiers with programmable gain and/or automatic gain control, bandpass filtering, and threshold detection circuitry to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

Cardiac signals are supplied to an analog-to-digital (A/D) data acquisition system 252, which is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The data acquisition system 252 is coupled to the microcontroller 220, or other detection circuitry, to assist in detecting an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 220 is further coupled to a memory 260 by a suitable data/address bus 262. The programmable operating parameters used by the microcontroller 220 are stored in memory 260 and used to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 allows intracardiac electrograms and status information relating to the operation of the device 100 (as contained in the microcontroller 220 or memory 260) to be sent to the external device 254 through an established communication link 266.

The memory 260 is also used to store apnea data pertaining to the recorded sleep apnea episodes, their measured durations, and the statistics derived from these episodes. The device uses the communication link 266 to upload this apnea data from the memory 260 to the external device 254. In particular, the device 100 transmits the apnea data and statistics to an external device 254, where the apnea data can be analyzed by an attending physician or other caregiver.

The implantable cardiac device 100 can further include one or more physiologic sensors 270. Such sensors are commonly referred to as "rate-responsive" sensors because they are typically used to adjust pacing stimulation rates according to the exercise state of the patient. However, the physiological sensor(s) 270 may further be used to detect changes in cardiac output, changes in the physiological condition of the heart, diurnal changes in activity (e.g., detecting sleep and wake states), or respiration activity (e.g., minute ventilation). The microcontroller 220 responds to changes sensed by the sensor(s) 270 by adjusting various pacing parameters (such as rate, AV Delay, V—V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient. Examples of physiologic sensors that may be implemented in device 100 include sensors that, for example, sense respiration activities, $O_2$ saturation, evoked response, pH of blood, and so forth.

In the illustrated implementation, the physiological sensors 270 include sensors for detecting patient activity and/or patient position and for detecting minute ventilation. Any sensor capable of sensing such changes, either directly or indirectly, may be used. In particular, the physiological sensors 270 include an activity/position sensor 272 to detect movement in the patient's position. The activity/position sensor 272 may be implemented in many ways, including as a 3 dimensional DC accelerometer. In one configuration, the accelerometer output signal is bandpass-filtered, rectified, and integrated at regular timed intervals. The processed accelerometer signal is used as a raw activity signal. The device derives an activity measurement based on the raw activity signal at intervals timed according to the cardiac cycle, then determines an activity variance parameter. One or both of the activity signal and the activity variance signal is used to detect patient state, for example, from among sleeping, waking, resting, and exercise state. A large activity variance signal is indicative of a prolonged exercise state. Low activity and activity variance signals are indicative of a prolonged resting state.

Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which is hereby incorporated by reference.

Another physiological sensor is a minute ventilation (MV) sensor 274 that is used to sense minute ventilation. Minute ventilation is the total volume of air that moves in and out of a patient's lungs in a minute. The MV sensor 274 uses transthoracic impedance, which is a measure of impedance across the chest cavity, to sense air movement. Lungs filled with air have higher impedance than empty lungs. Thus, upon inhalation, impedance increases and upon exhalation, impedance decreases.

Still another possible physiological sensor is an $O_2$ sensor 275, which measures oxygen-related parameters. Such a sensor may be positioned in the right ventricle, or atrial line, and measure such things as $O_2$ saturation, $O_2$ pressure, or $SO_2$ values.

Signals generated by the position sensor 272, MV sensor 274, and $O_2$ sensor 275 are passed to the microcontroller 220 for analysis by the sleep apnea detector 238. Such signals can be used to determine whether the patient is at rest, whether the patient is experiencing an episode of sleep apnea, when to begin measuring a duration of a sleep apnea episode, and whether to invoke any responsive therapy prescribed by the sleep apnea therapy module 240.

The implantable cardiac device 100 additionally includes a battery 276 that provides operating power to all of the components shown in FIG. 2. The battery 276 is capable of operating at low current drains for long periods of time (e.g., less than 10 μA), and is capable of providing high-current pulses (for capacitor charging) when the patient requires a shock pulse (e.g., in excess of 2 A, at voltages above 2 V, for periods of 10 seconds or more). The battery 276 also desirably has a predictable discharge characteristic so that elective replacement time can be detected. As one example, the device 100 employs lithium/silver vanadium oxide batteries.

The device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement; detecting operable electrodes and automatically switching to an operable pair if dislodgement occurs; measuring thoracic impedance for determining shock thresholds; detecting when the device has been implanted; measuring stroke volume; and detecting the opening of heart valves; and so forth. In particular relevance to our ongoing discussion, the impedance measuring circuit 278 can be used to measure respiration-related parameters, such as respiration rate, minute ventilation, respiration signal amplitude, and tidal volume. The impedance measuring circuit 278 is coupled to the switch 226 so that any desired electrode may be used.

The device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 Joules), moderate (e.g., 0.5–10 Joules), or high energy (e.g., 11 to 40 Joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Sleep Apnea Duration Measurement

Figure 3:
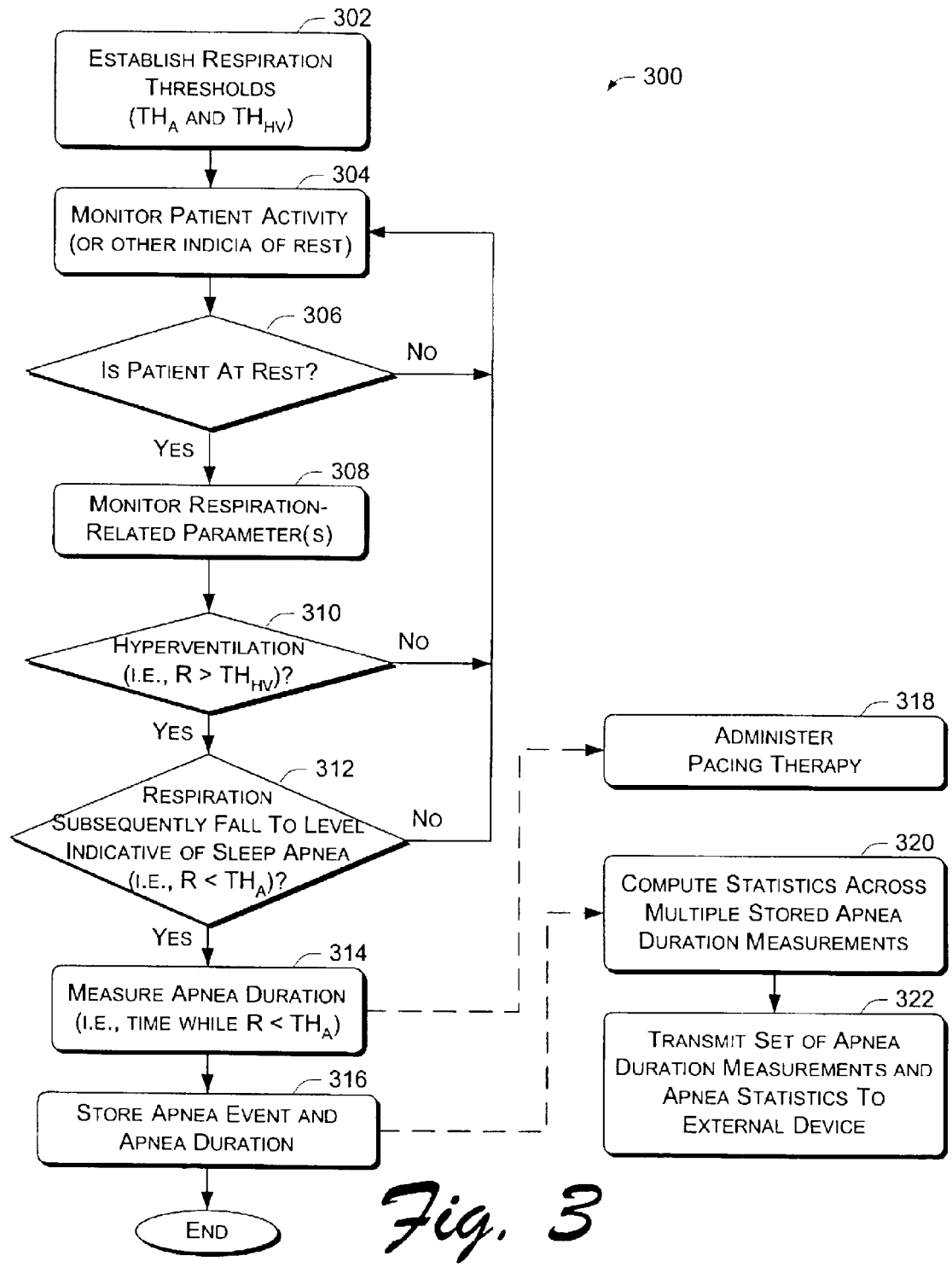
FIG. 3 is a flow diagram of a process for detecting an episode of sleep apnea using a respiration parameter and measuring the duration of the episode.

FIG. 3 shows a process 300 for detecting and measuring sleep apnea episodes. This process 300 may be implemented in connection with any suitably configured device, although it will be described as being executed by the implantable cardiac device 100 of FIGS. 1 and 2. In the flow diagram, the operations are summarized in individual blocks. The operations may be performed in hardware and/or as machine-readable instructions (software or firmware) that can be executed by a processor.

At block 302, respiration thresholds used by the process to detect sleep apnea are set. In the described example, two respiration thresholds for amplitude of a respiration signal, tidal volume signal, or other respiration-related signal are employed such as MV: (1) a first or high threshold $TH_{HV}$, which is used to determine when a patient enters a state of hyperventilation; and (2) a second or low threshold $TH_A$, which is used to describe when a patient enters an episode of sleep apnea following the state of hyperventilation. As one example implementation, histograms may be used to determine the threshold levels. During normal breathing, the device constructs the tidal volume (or UV) histogram and then periodically calculates the mean and standard deviation of tidal volume or MV histograms. The hyperventilation threshold $TH_{HV}$ is then set to the mean plus a multiple of the standard deviation (e.g., 2×), while the apnea threshold $TH_A$ is set to the mean minus a multiple of the standard deviation.

At blocks 304 and 306, the implantable cardiac therapy device 100 monitors patient activity and/or respiration to determine whether the patient is at rest. There are many ways to implement this function. One approach is to monitor the activity sensor 272 and confirm that a patient is at rest when the patient has been inactive for a predetermined amount of time. Another approach is to monitor signals from an accelerometer-based position/motion sensor 272 to identify when the patient stops moving for a prolonged period of time, or when the patient reclines to a supine position. So long as the patient is not resting (i.e., the "No" branch from block 306), the device continues to monitor patient activity.

Once the patient is determined to be at rest (i.e., the "Yes" branch from block 306), the device monitors one or more respiration-related parameters associated with or indicative of the patient's respiration (block 308). This may be done in many ways, including measuring respiration rate, tidal volume, minute ventilation, $O_2$ saturation and so on. The device monitors such respiration-related parameters using, for example, one or more physiological sensor 270 impedance sensor and measuring circuit 278.

Figure 4:
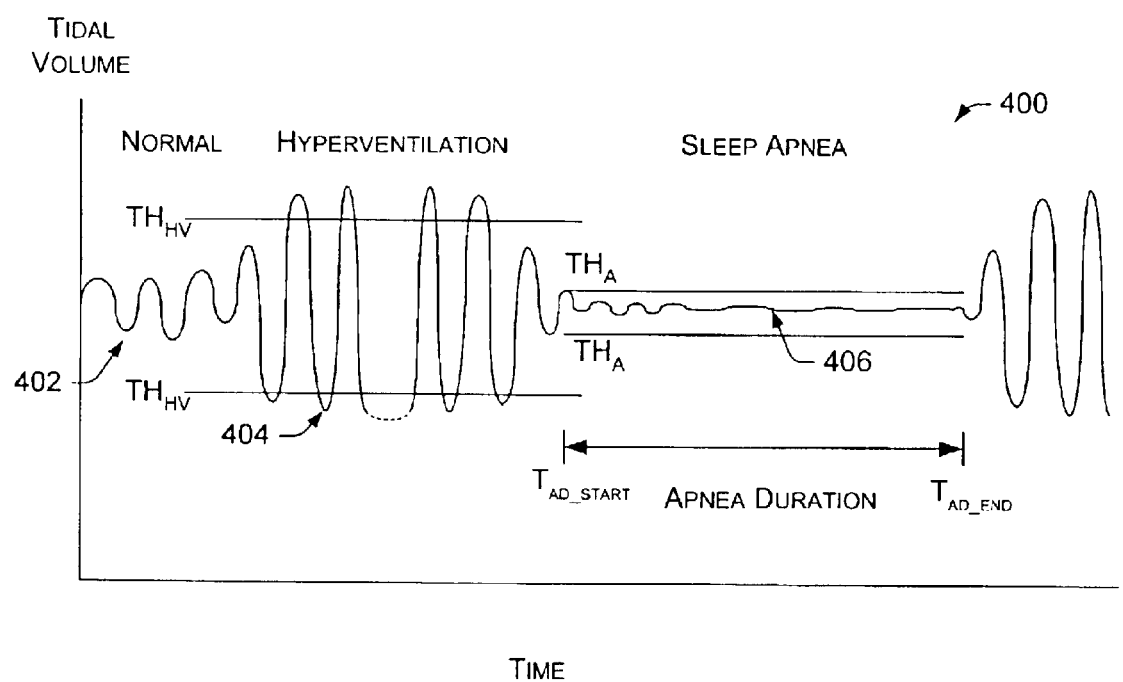
FIG. 4 shows a respiratory signal pattern that may be used to detect when a patient is experiencing a sleep apnea episode.

The device is capable of differentiating among normal breathing patterns, hyperventilation patterns, and apnea patterns. For purposes of continuing discussion, the device will be described as monitoring a respiration signal representative of tidal volume. The thresholds $TH_{HV}$ and $TH_A$ are set to predetermined amplitude levels of the tidal value that are suggestive of hyperventilation and sleep apnea. FIG. 4 illustrates an exemplary respiration signal pattern 400 to show the various phases of respiration. Initially, the patient is exhibiting normal respiration patterns, as represented by signal pattern 402. The patient then enters a hyperventilation pattern in which the tidal volume exceeds the hyperventilation threshold $TH_{HV}$, as represented by signal pattern 404. Following the hyperventilation pattern, the user experiences an episode of sleep apnea in which the tidal volume falls below the apnea threshold $TH_A$, as presented by pattern 406.

With reference to block 310 in FIG. 3, the device determines whether the patient enters a state of hyperventilation, which is indicated when the respiration signal R exceeds the hyperventilation threshold $TH_{HV}$. This condition is illustrated by pattern 404 in FIG. 4. The determination may return a positive when the threshold is exceeded for the first time, or alternatively, when the threshold is exceeded a predetermined number of times within a prescribed time period. If there is no indication of hyperventilation (i.e., the "No" branch from block 310), the device continues to confirm that the user is at rest and to monitor the patient's respiration.

Conversely, if the patient undergoes hyperventilation (i.e., the "Yes" branch from block 310), the device next ascertains whether the respiration signal R subsequently drops below the minimum apnea threshold $TH_A$, as an indication that the patient is experiencing an episode of sleep apnea (block 312). This condition is represented by pattern 406 in FIG. 4. The sleep apnea detector 238 can be configured to confirm an apnea condition when the respiration signal stays within the range set by threshold $TH_A$ for a predetermined time period, number of respiration cycles, or the like. Typically, a patient who is experiencing a sleep apnea episode will exhibit a very low to no respiratory activity for periods of 30 to 60 seconds. Hence, the detector 238 may be programmed to return a positive when the respiration signal fails to exceed the apnea threshold $TH_A$ for a period of 10–20 seconds. If there is no prolonged period of low respiration activity following hyperventilation (i.e., the "No" branch from block 312), the device continues to confirm that the user is at rest and to monitor the patient's respiration.

If the device confirms an episode of sleep apnea (i.e., the "Yes" branch from block 312), the duration measurement module 242 of sleep apnea detector 238 measures the duration of the sleep apnea episode (block 314). The measurement module 242 times how long the respiration signal remains below the apnea threshold $TH_A$. The apnea duration is measured from the time that the respiration signal last crosses the apnea threshold $TH_A$ before a prolonged period (e.g., 30–60 sec) until the time that the respiration signal once again crosses the apnea threshold $TH_A$. The duration may be measured while the patient is experiencing the apnea episode, or after the episode has concluded.

The measured duration is shown in FIG. 4. The apnea duration start time $T_{AD\_START}$ is set when the respiration signal last crosses through the apnea threshold $TH_A$ just before a prolonged period in which the signal fails to exceed the apnea threshold. The apnea duration end time $T_{AD\_END}$ is set when the respiration signal once again exceeds the apnea threshold $TH_A$. The apnea duration is the period between $T_{AD\_START}$ and $T_{AD\_END}$.

At block 316 in FIG. 3, the cardiac device 100 stores the apnea event and measured apnea duration in memory 260. The stored events and measured durations can then be transmitted to the external device 254 for analysis by a physician.

As indicated by block 318, the device 100 can be optionally configured to administer pacing therapy in response to detection of the sleep apnea episode. For instance, one possible pacing response is to apply overdrive pacing, where the pacing rate is increased by a fixed amount above an intrinsic rate usually applied when the patient is at rest. As an alternative to increasing the pacing rate by a fixed amount, the device may be programmed to adjust the overdrive pacing rate using some target parameter. The overdrive pacing may be applied for a predetermined time period, or number of beats. It may then be gradually reduced.

Once the device collects multiple episodes of sleep apnea, the cardiac device 100 may be further configured to compute statistics on the recorded episodes (block 320). Suppose, for example, that the device collects durations for multiple sleep apnea episodes that occurred over some preset time period (e.g., 24 hours, while patient is at rest, etc.). The statistical module 243 could then derive an average duration for the multiple episodes and/or a total duration of all episodes during the time period. At block 322, the device transmits the duration measurements and the statistics to the external device for diagnosis by a physician or attending caregiver.

Apnea duration(s) for each episode, average apnea duration, and total apnea duration could prove useful to physicians who are trying to better understand sleep apnea in individual patients. Currently, physicians rely on the apnea hypopnea index (AHI) as a standard index for describing the severity of sleep apnea. With this measure, however, apnea periods with different duration are counted equally. Apnea duration may provide a more sensitive measure for describing the severity. Furthermore, the apnea duration diagnostics may be used to evaluate different forms of therapies to determine which therapies are effective at reducing sleep apnea. Evaluation of pacing therapies, in particular, is described in the following section.

Figure 5:
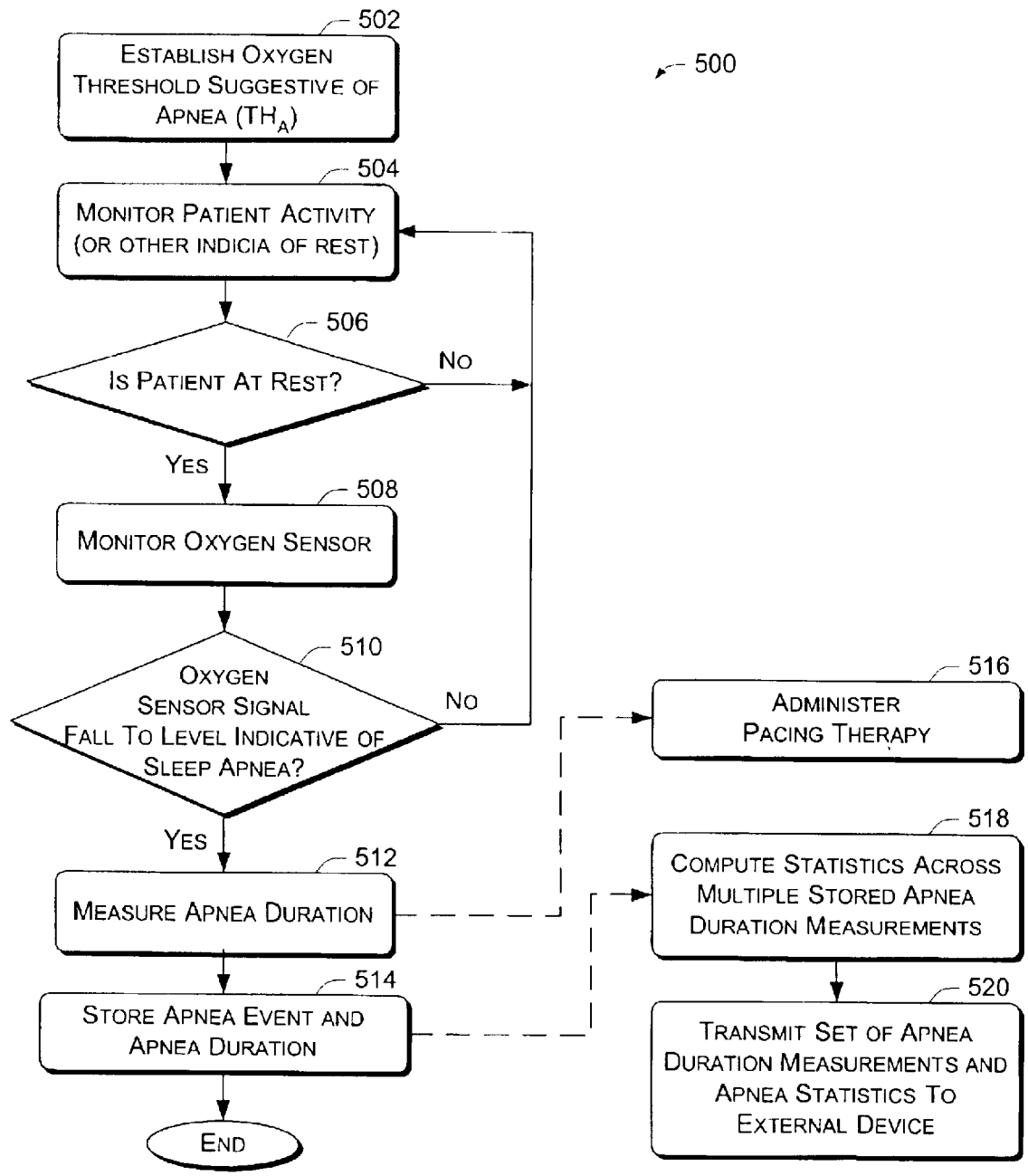
FIG. 5 is a flow diagram of a process for detecting an episode of sleep apnea using an oxygen parameter and measuring the duration of the episode.

FIG. 5 shows an alternative process 500 for detecting and measuring sleep apnea episodes that uses an $O_2$ sensor reading. In process 300 of FIG. 3, respiration parameters used to detect hyperventilation and subsequent apnea conditions were used. This process for detecting apnea is effective for the case of central sleep apnea. Process 500 employs an $O_2$ sensor reading, such as $O_2$ saturation, as a way to detect apnea conditions in the case of obstructive sleep apnea. As above, this process 500 may be implemented in connection with any suitably configured device, although it will be described as being executed by the implantable cardiac device 100 of FIGS. 1 and 2. The operations may be performed in hardware and/or as machine-readable instructions (software or firmware) that can be executed by a processor.

At block 502, an $O_2$ threshold used by the process to detect sleep apnea is set. One suitable threshold $TH_A$ is used to describe an $O_2$ level that is suggestive of sleep apnea. During normal conditions, the device constructs a histogram of a particular $O_2$ reading ($O_2$ saturation, $SO_2$, $O_2$ pressure, etc.) and then periodically calculates the mean and standard deviation of it. The threshold $TH_A$ is then set to the mean minus a multiple of the standard deviation.

At blocks 504 and 506, the implantable cardiac therapy device 100 monitors patient activity and/or respiration to determine whether the patient is at rest. Once the patient is determined to be at rest (i.e., the "Yes" branch from block 506), the device monitors an oxygen sensor, such as $O_2$ saturation, $O_2$ pressure, and so on (block 508).

At block 510, the device determines whether the oxygen-related signal falls a below the apnea threshold $TH_A$. If not (i.e., the "No" branch from block 510), the device continues to confirm that the user is at rest and to monitor the patient's respiration. Conversely, if the device confirms an episode of sleep apnea as indicated by the oxygen reading (i.e., the "Yes" branch from block 510), the duration measurement module 242 of sleep apnea detector 238 measures the duration of the sleep apnea episode (block 512). The measurement module 242 times how long the oxygen signal remains below the apnea threshold $TH_A$. The apnea duration is measured from the time that the oxygen signal last crosses the apnea threshold $TH_A$ before a prolonged period (e.g., 30–60 sec) until the time that the oxygen signal once again crosses the apnea threshold $TH_A$. The duration may be measured while the patient is experiencing the apnea episode, or after the episode has concluded.

At block 514, the cardiac device 100 stores the apnea event and measured apnea duration in memory 260. The stored events and measured durations can then be transmitted to the external device 254 for analysis by a physician.

At block 516, the device 100 can be optionally configured to administer pacing therapy in response to detection of the sleep apnea episode. Once the device collects multiple episodes of sleep apnea, the cardiac device 100 may be further configured to compute statistics on the recorded episodes (block 518). Suppose, for example, that the device collects durations for multiple sleep apnea episodes that occurred over some preset time period (e.g., 24 hours, while patient is at rest, etc.). The statistical module 243 could then derive an average duration for the multiple episodes and/or a total duration of all episodes during the time period. At block 520, the device transmits the duration measurements and the statistics to the external device for diagnosis by a physician or attending caregiver.

Therapy Evaluation

As shown in block 318 of FIG. 3 and block 516 in FIG. 5, the cardiac device can be programmed to administer a pacing therapy in response to detecting sleep apnea. In addition, the device may be programmed, under supervision of a physician, to apply different types of pacing therapies on a patient to determine which therapies are effective at lessening the average apnea duration or total apnea duration.

Figure 6:
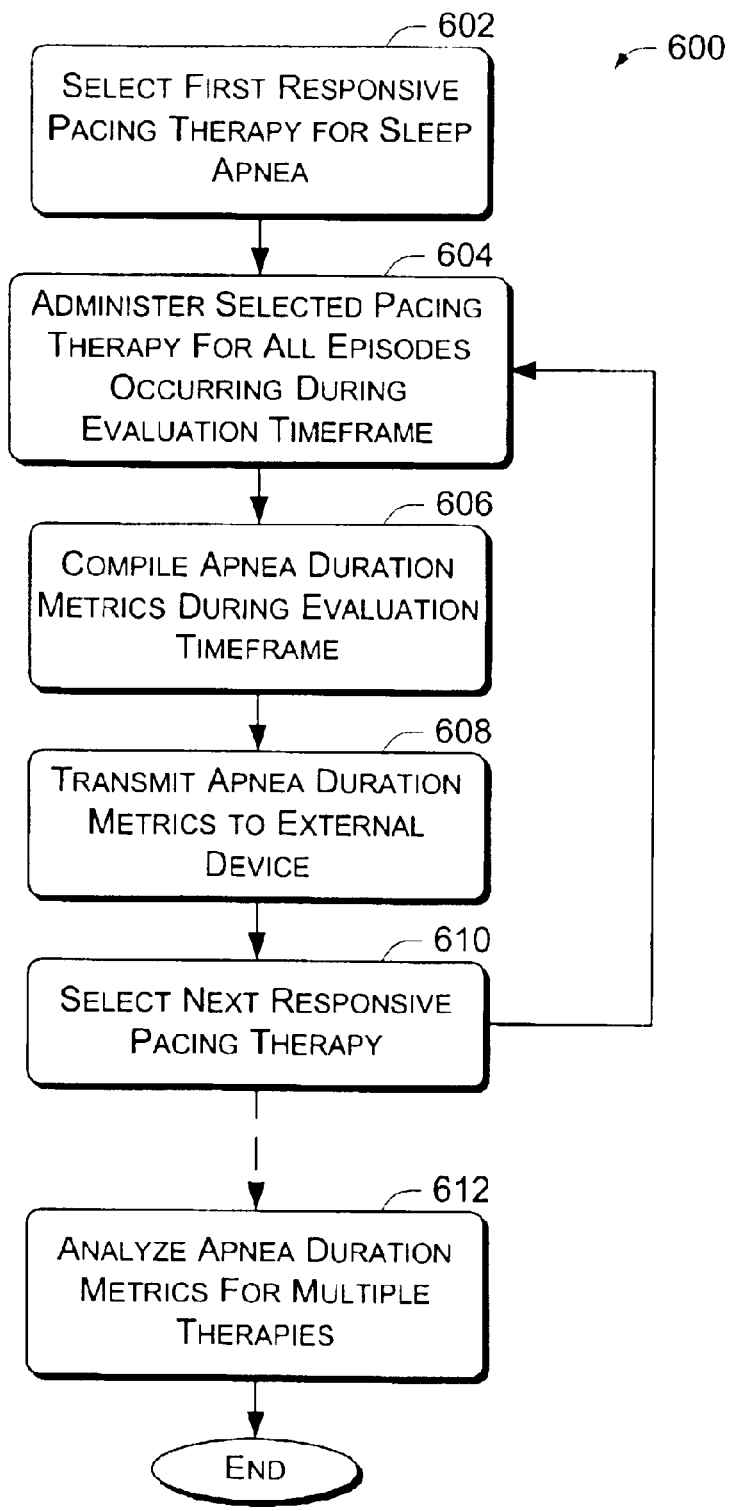
FIG. 6 is a flow diagram of a process for selecting a suitable pacing therapy by trying different pacing therapies and analyzing their impact on apnea duration.

FIG. 6 shows a process 600 for evaluating different pacing therapies in regards to their impact on apnea duration. As above, the evaluation process 600 will be described as being executed by the implantable cardiac device 100 of FIGS. 1 and 2. The operations may be performed in hardware and/or as machine-readable instructions (software or firmware) that can be executed by a processor.

At block 602, a first pacing therapy is selected under the direction of the physician. The pacing therapy may be pre-stored on the device, or programmed a into the device for purposes of evaluation. At block 604, the sleep apnea therapy module 240 administers the selected pacing therapy for all episodes of sleep apnea that occur during a predefined evaluation timeframe. The evaluation timeframe may be of any duration prescribed by the physician, with example timeframes being a 24 hour period or a week.

At block 606, the device 100 compiles apnea duration metrics (e.g., average apnea duration, total apnea duration) for all episodes that occur during the evaluation timeframe. The device measures duration of each episode, stores the duration, and subsequently computes statistical information on the apnea duration data, such as average and total durations. The apnea duration metrics are transmitted to the physician for review (block 608).

At block 610, a new pacing therapy is selected under the direction of the physician. For instance, the device may utilize another pre-stored therapy 245 or the physician may download another therapy into the device for the next trial. Process flow then returns to block 504, where the device administers the next selected pacing therapy for all episodes occurring in the evaluation timeframe.

At block 612, the apnea duration metrics collected for multiple different therapies are analyzed to determine which of the therapies is most effective at shortening the apnea duration. This analysis is performed, for example, on an external computing system, such as a programmer or other computer used by the physician. However, as memory and processing capabilities continue to improve, the analysis may be conducted at the implantable cardiac device for multiple different pacing therapies.

CONCLUSION

The foregoing discussion describes use of apnea duration metrics, derived by the implantable cardiac device, to discern severity of sleep apnea and to help evaluate whether various pacing therapies are effective for treating sleep apnea. With such techniques, effective therapies for treating apnea can be developed on a patient-by-patient basis.

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. An implantable cardiac device comprising:

sensing circuitry to sense whether a patient is at rest;

a sleep apnea detector to detect when a patient, who is at rest, is experiencing an episode of sleep apnea and to measure a duration of the episode of sleep apnea;

a therapy module to prescribe a pacing therapy for treating sleep apnea from among multiple different pacing therapies;

a pulse generator to generate pacing pulses according to the prescribed pacing therapy for an evaluation timeframe; and the sleep apnea detector measuring durations of episodes experienced during the evaluation timeframe of the prescribed pacing therapy.

2. An implantable cardiac device as recited in claim 1, wherein the sensing circuitry comprises an activity sensor to sense a patient's activity to determine whether the patient is at rest.

3. An implantable cardiac device as recited in claim 1, wherein the sensing circuitry comprises a position sensor to sense a patient's position as a way to determine whether the patient is at rest.

4. An implantable cardiac device as recited in claim 1, wherein the sensing circuitry comprises an accelerometer that is used to determine whether the patient is at rest.

5. An implantable cardiac device as recited in claim 1, wherein the sensing circuitry is configured to sense a respiration-related signal and the sleep apnea detector detects the episode of sleep apnea based upon the respiration-related signal.

6. An implantable cardiac device as recited in claim 5, wherein the sensing circuitry comprises an impedance sensor to detect the respiration-related signal.

7. An implantable cardiac device as recited in claim 5, wherein the respiration-related signal is selected from a group of signals comprising a signal indicative of tidal volume, a signal indicative of respiration rate, and a signal indicative of minute ventilation, and $O_2$ saturation.

8. An implantable cardiac device as recited in claim 5, wherein the sleep apnea detector is configured to detect the episode of sleep apnea by determining when the respiration-related signal exceeds a first threshold indicative of hyperventilation and then falls below a lower second threshold for a predetermined time period.

9. An implantable cardiac device as recited in claim 1, wherein the sensing circuitry is configured to sense an oxygen-related signal and the sleep apnea detector detects the episode of sleep apnea based upon the oxygen-related signal.

10. An implantable cardiac device as recited in claim 1, further comprising a memory to store apnea data pertaining to the episode of sleep apnea and the duration of the episode.

11. An implantable cardiac device as recited in claim 1, further comprising a statistical module to derive statistics on the duration of the sleep apnea episode.

12. An implantable cardiac device as recited in claim 1, further comprising a pulse generator to generate pacing pulses applied in response to the sleep apnea detector detecting the episode of sleep apnea.

13. A method implemented by an implantable cardiac device, comprising:

detecting an episode of sleep apnea;

determining a duration of the sleep apnea episode;

stimulating a heart in response to at least selected episodes of sleep apnea;

administering multiple different pacing therapies to treat the sleep apnea; and evaluating the pacing therapies based on how the pacing therapies affect the duration of the sleep apnea episodes.

14. An implantable cardiac device comprising:

a rest-indicating sensor to sense whether a patient is at rest;

a respiration sensor to sense respiration;

a processor to confirm that a patient is at rest based on data from the rest-indicating sensor and while the patient is resting, to detect an episode of sleep apnea based on changes in the respiration, the processor being further configured to measure a duration of the episode of sleep apnea; and a memory to store apnea data pertaining to the episode of sleep apnea and the duration of the episode;

wherein the processor is configured to detect the episode of sleep apnea in an event that the respiration exceeds a first threshold indicative of hyperventilation and then falls below a lower second threshold for a predetermined time period and wherein the processor measures the duration of the episode of sleep apnea as a time period starting when the respiration falls below the second threshold until and ending when the respiration once again exceeds the second threshold.

15. An implantable cardiac device as recited in claim 14, wherein the rest-indicating sensor comprises at least one of an activity sensor, a position sensor, or an accelerometer.

16. An implantable cardiac device as recited in claim 14, wherein the respiration sensor comprises an impedance sensor configured as a minute ventilation sensor.

17. A method comprising:

administering multiple different pacing therapies to treat sleep apnea using an implantable cardiac device, such that each pacing therapy is administered to treat all episodes of sleep apnea that occur within a corresponding evaluation timeframe;

compiling duration metrics pertaining to duration of the sleep apnea episodes; and analyzing the duration metrics to evaluate how effective the different pacing therapies are at treating the sleep apnea.

18. A method as recited in claim 17, wherein the compiling comprises:

measuring duration of each sleep apnea episode; and computing at least one of total apnea duration and average apnea duration of all sleep apnea episodes that occur within the corresponding evaluation timeframe.

19. A method as recited in claim 17, further comprising transmitting the duration metrics to an external device and performing the analyzing at the external device.

20. An implantable cardiac device comprising:

a rest-indicating sensor to sense whether a patient is at rest;

a respiration sensor to sense respiration;

a processor to confirm that a patient is at rest based on data from the rest-indicating sensor and while the patient is testing, to detect an episode of sleep apnea based on changes in the respiration, the processor being further configured to measure a duration of the episode of sleep apnea; and a memory to store apnea data pertaining to the episode of sleep apnea and the duration of the episode;

wherein the processor stores apnea data for multiple episodes and computes statistics on the apnea data and wherein the processor derives an average duration and a total duration of the multiple episodes.

21. An implantable cardiac device as recited in claim 20, further comprising a pulse generator to generate pacing pulses applied in response to the sleep apnea.

22. An implantable and programmable cardiac device having a memory and a processor, the cardiac device being programmed to perform tasks comprising:

sensing an oxygen-related parameter;

detecting an episode of sleep apnea in an event that the oxygen-related parameter falls below a threshold for a predetermined time period suggestive of apnea; and measuring a duration of the episode of steep apnea taken from a start time when the oxygen-related parameter first falls below the threshold until an end time when the oxygen-related parameter subsequently rises above the threshold.

23. An implantable and programmable cardiac device as recited in claim 22, further programmed to perform tasks comprising:

storing durations measured for multiple apnea episodes; and computing at least one of an average duration and a total duration from the multiple episodes.

24. An implantable and programmable cardiac device as recited in claim 22, further programmed to perform tasks comprising applying an increased rate of pacing pulses in response to detecting onset of sleep apnea.

25. An implantable cardiac device comprising:

a rest-indicating sensor to sense whether a patient is at rest;

an oxygen sensor to sense $O_2$ saturation;

a processor to confirm that a patient is at rest based on data from the rest-indicating sensor and while the patient is resting, to detect an episode of sleep apnea based on changes in the $O_2$ saturation, the processor being further configured to measure a duration of the episode of sleep apnea; and a memory to store apnea data pertaining to the episode of sleep apnea and the duration of the episode;

wherein the processor is configured to detest the episode of sleep apnea in an event that the $O_2$ saturation falls below a threshold for a predetermined time period and wherein the processor measures the duration of the episode of sleep apnea as a time period starting when the $O_2$ saturation falls below the threshold until and ending when the $O_2$ saturation once again exceeds the threshold.

26. An implantable cardiac device as recited in claim 25, wherein the processor stores apnea data for multiple episodes and computes statistics on the apnea data.

27. An implantable cardiac device comprising:

a rest-indicating sensor to sense whether a patient is at rest;

an oxygen sensor to sense $O_2$ saturation;

a processor to confirm that a patient is at rest based on data from the rest-indicating sensor and while the patient is resting, to detect an episode of sleep apnea based on changes in the $O_2$ saturation, the processor being further configured to measure a duration of the episode of sleep apnea;

a memory to store apnea data pertaining to the episode of sleep apnea and the duration of the episode a therapy module to prescribe a pacing therapy for treating sleep apnea from among multiple different pacing therapies;

a pulse generator to generate pacing pulses according to the prescribed pacing therapy for an evaluation timeframe; and the sleep apnea detector measuring durations of episodes experienced during the evaluation timeframe of the prescribed pacing therapy.

28. A method implemented by an implantable cardiac device, comprising:

detecting an episode of sleep apnea;

determining a duration of the sleep apnea episode; and stimulating a heart in response to at least selected episodes of sleep apnea;

wherein the detecting comprises determining when a respiration signal exceeds a first threshold indicative of hyperventilation and then falls below a lower second threshold for a predetermined period of time and wherein the determining comprises measuring the duration from a start time when the respiration signal falls below the second threshold until an end time when the respiration signal rises above the second threshold.

29. A method as recited in claim 28, wherein the detecting comprises monitoring a respiration signal for a pattern of hyperventilation followed by minimal respiration activity.

30. A method as recited in claim 28, wherein the detecting comprises monitoring an oxygen-related parameter and determining when the oxygen-related parameter falls below a threshold of minimal oxygen content for a predetermined time period.

31. A method as recited in claim 28, further comprising:

storing durations of multiple episodes of sleep apnea; and computing one or more statistics on the durations of the multiple episodes.

32. A method as recited in claim 28, further comprising administering pacing therapy in response to detecting the episode of sleep apnea.

33. A method comprising:

determining that a patient is at rest;

monitoring a respiration signal;

detecting an episode of sleep apnea in an event that, while the patient is at rest, the respiration signal exceeds a first threshold associated with hyperventilation and then falls below a lower second threshold for a predetermined time period suggestive of apnea;

measuring a duration of the episode of sleep apnea; and storing the duration of the sleep apnea;

wherein measuring comprises timing the duration from a start time when the respiration signal first falls below the second threshold until an end time when the respiration signal subsequently rises above the second threshold.

34. A method as recited in claim 33, wherein the determining comprises monitoring the patient's position to determine if the patient is in a supine position.

35. A method as recited in claim 33, wherein the determining comprises monitoring patient activity.

36. A method as recited in claim 33, further comprising:
storing durations of multiple episodes of sleep apnea; and
computing one or more statistics on the durations of the multiple episodes.

37. A method as recited in claim 33, further comprising administering pacing therapy in response to the onset of sleep apnea.

38. An implantable and programmable cardiac device having a memory and a processor, the cardiac device being programmed to perform tasks comprising:
detecting when a patient is experiencing an episode of sleep apnea;
determining a duration of the sleep apnea episode; and
stimulating a heart in response to at least selected episodes of sleep apnea;
storing durations measured for multiple apnea episodes; and
computing at least one of an average duration and a total duration from the multiple episodes.

39. An implantable and programmable cardiac device as recited in claim 38, further programmed to perform tasks comprising applying an increased rate of pacing in response to detecting onset of sleep apnea.

40. An implantable and programmable cardiac device having a memory and a processor, the cardiac device being programmed to perform tasks comprising:
sensing a respiration signal;
detecting an episode of sleep apnea in an event that the respiration signal exceeds a first threshold associated with hyperventilation followed by falling below a lower second threshold for a predetermined time period suggestive of apnea; and
measuring a duration of the episode of sleep apnea taken from a start time when the respiration signal first falls below the second threshold until an end time when the respiration signal subsequently rises above the second threshold.

41. An implantable and programmable cardiac device as recited in claim 40, further programmed to perform tasks comprising:
storing durations measured for multiple apnea episodes; and
computing at least one of an average duration and a total duration from the multiple episodes.

42. An implantable and programmable cardiac device as recited in claim 40, further programmed to perform tasks comprising applying an increased rate of pacing pulses in response to detecting onset of sleep apnea.

43. An implantable cardiac device comprising:
a rest-indicating sensor to sense whether a patient is at rest;
a respiration sensor to sense respiration;
a processor to confirm that a patient is at rest based on data from the rest-indicating sensor and while the patient is resting, to detect an episode of sleep apnea based on changes in the respiration, the processor being further configured to measure a duration of the episode of sleep apnea;
a memory to store apnea data pertaining to the episode of sleep apnea and the duration of the episode;
a therapy module to prescribe a pacing therapy for treating sleep apnea from among multiple different pacing therapies;
a pulse generator to generate pacing pulses according to the prescribed pacing therapy for an evaluation timeframe; and
the sleep apnea detector measuring durations of episodes experienced during the evaluation timeframe of the prescribed pacing therapy.

44. A system comprising:
an implantable cardiac device configured to detect episodes of sleep apnea and to administer different pacing therapies for treating the sleep apnea, the implantable cardiac device being further configured to collect duration metrics pertaining to durations of sleep apnea episodes measured for the different pacing therapies and to export the duration metrics to an external computing device; and
a computing system to analyze the duration metrics collected by the implantable cardiac device.

45. A system as recited in claim 44, wherein the implantable cardiac device comprises:
a sensor to sense a respiration signal; and
a processor programmed to detect an episode of sleep apnea in an event that the respiration signal exceeds a first threshold associated with hyperventilation followed by falling below a lower second threshold for a predetermined time period suggestive of apnea, the processor measuring the duration between a start time when the respiration signal first falls below the second threshold and an end time when the respiration signal subsequently rises above the second threshold.

46. A system as recited in claim 44, wherein the implantable cardiac device comprises:
an oxygen sensor to sense an oxygen-related parameter; and
a processor programmed to detect an episode of sleep apnea in an event that the oxygen-related parameter falls below a threshold for a predetermined time period suggestive of apnea, the processor measuring the duration between a start time when the oxygen-related parameter first falls below the threshold and an end time when the oxygen-related parameter subsequently rises above the threshold.

47. A system as recited in claim 44, wherein the implantable cardiac device computes statistics on the duration metrics collected for each pacing therapy and stores the statistics for export to the external computing device.

48. A system as recited in claim 44, wherein the implantable cardiac device administers each pacing therapy for a predefined evaluation timeframe and the computer system analyzes the duration metrics collected for the different pacing therapies to identify one or more therapies that are effective at treating sleep apnea.

* * * * *